United States Patent [19]

Strong et al.

[11] 3,940,458

[45] Feb. 24, 1976

[54] 1-CARBAMOYL VINYL PHOSPHATES

[75] Inventors: Jerry G. Strong, Fanwood; Roger P. Napier, Somerville, both of N.J.

[73] Assignee: Mobil Oil Corporation, New York, N.Y.

[22] Filed: Jan. 10, 1973

[21] Appl. No.: 322,316

Related U.S. Application Data

[63] Continuation-in-part of Ser. No. 230,475, Feb. 29, 1972, abandoned.

[52] U.S. Cl. .... 260/943; 260/247.2 A; 260/293.89; 260/310 A; 260/326.5 A; 260/935; 260/938; 260/940; 260/944; 260/945; 424/211
[51] Int. Cl.²........................................... C07F 9/113
[58] Field of Search ........... 260/943, 944, 935, 938, 260/940, 941, 945

[56] References Cited
UNITED STATES PATENTS

| | | |
|---|---|---|
| 3,055,798 | 9/1962 | Beriger .......................... 260/943 X |
| 3,068,268 | 12/1962 | Tieman et al. .................. 260/943 X |
| 3,068,271 | 12/1962 | Tieman .......................... 260/943 X |
| 3,784,589 | 1/1974 | Large ............................. 260/943 X |
| 3,787,536 | 1/1974 | Bayer et al. ...................... 260/943 |

*Primary Examiner*—Richard L. Raymond
*Attorney, Agent, or Firm*—Charles A. Huggett; Howard M. Flournoy

[57] ABSTRACT

1-Carbamoylvinyl phosphates and phosphonates are novel compounds which provide an effective means for controlling insects.

10 Claims, No Drawings

1-CARBAMOYL VINYL PHOSPHATES

CROSS-REFERENCE TO RELATED APPLICATIONS

This application is a continuation-in-part of copending application Ser. No. 230,475, filed Feb. 29, 1972 and now abandoned.

BACKGROUND OF THE INVENTION:

1. FIELD OF THE INVENTION

This invention is directed to novel 1-carbamoylvinyl phosphate compounds. This invention also relates to methods and compositions of matter for controlling pests, insects particularly.

2. DESCRIPTION OF PRIOR ART

A few related series of compounds are known in the patent literature, for example, U.S. Pat. Nos. 2,908,605 and 2,956,073 describe certain chlorovinyl phosphates and disclose their utility as insecticides. However, the prior art does not disclose chlorovinyl phosphates in which a carbamoyl group is attached alpha to the phosphate group, i.e. attached to the same carbon atom as the phosphate group. In the compounds according to this invention carbamoyl groups alpha to the phosphate group, as shown herein below, are highly effective against various stages of insect development.

SUMMARY OF THE INVENTION

This invention provides novel 1-carbamoylvinyl phosphates for use in controlling pests. These new compounds are thus valuable agents for combatting pests, especially insects. They are highly effective against various stages of insect development, such as pupae, larvae and adults. These compounds combat insects through both systemic and direct contact action. Because a systemic insecticide must be absorbed through the plant roots and translocated to all parts of the plant, few insecticides are found to be systemic. The compounds act both as stomach poisons and contact poisons.

This invention further provides for insect controlling compositions comprising at least one such compound and an inert solid or liquid carrier therefor. The invention also relates to methods of using these compounds and/or compositions in insect control procedures.

DESCRIPTION OF SPECIFIC EMBODIMENTS

The invention provides new 1-carbamoylvinyl phosphates of the following general structure:

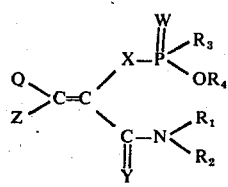

They may exist in either the cis or trans stereochemical form (i.e. when $Q \neq Z$). The present invention includes compounds of both structures and also mixtures thereof. Whenever only one of these forms is given, it is to be understood that the other form is included, provided it is capable of existing.

In the above formula X, Y and W represent oxygen or sulfur; $R_1$, $R_2$, $R_3$ and $R_4$ represent a radical selected from the group consisting of hydrogen, branched or unbranched alkyl ($C_1$–$C_8$), cycloalkyl ($C_3$–$C_8$), alkenyl ($C_2$–$C_8$), alkoxy ($C_1$–$C_8$), aryl, aralkyl ($C_7$–$C_{14}$), acetyl, carbalkoxy, alkylmercapto ($C_1$–$C_8$) carbamoyl (mono and dialkyl) and combinations of these as parts of the same radical, which radical may have substituted thereon a member or members of the group consisting of hydroxy, halogen, alkoxy, cyano, carbalkoxy and combinations and multiples of these; $R_1$ and $R_2$ together with the nitrogen atom may form a ring system containing 5 or 6 ring members; and Q and Z represent a radical selected from the group consisting of $R_1$, $R_2$, $R_3$ and $R_4$ and/or from the group consisting of halogen (Cl, Br, F), cyano, and alkylsulfonyl.

Non-limiting examples of compounds included in this invention are:

Dimethyl 2,2-Dichloro-1-(dimethylcarbamoyl)vinyl Thiophosphate

Diethyl 2-Chloro-2-methyl-1-(dimethylcarbamoyl)-vinyl Thiophosphate

Dimethyl 2,2-Dichloro-1-(piperidinocarbonyl)vinyl Phosphate

Dimethyl 2,2-Dichloro-1-(pyrazolocarbonyl)vinyl Phosphate

Dimethyl 2,2-Dichloro-1-(2-oxopyrrolidinocarbonyl)vinyl Phosphate

Dimethyl 2-Chloro-1-(morpholinocarbonyl)vinyl Phosphate

Dimethyl 2-Chloro-1-(dimethylcarbamoyl)vinyl Thiophosphate

Dimethyl 1-(Dimethylcarbamoyl)vinyl Thiophosphate

Dimethyl 2-Methyl-1-(dimethylcarbamoyl)vinyl Thiophosphate

Dimethyl 1-(Dimethylcarbamoyl)vinyl Dithiophosphate

Dimethyl 2-Chloro-1-(dimethylthiocarbamoyl)vinyl Phosphate

Dimethyl 1-(Dimethylthiocarbamoyl)vinyl Phosphate

Dimethyl 1-(N-Methylthiocarbamoyl)vinyl Phosphate

Dimethyl 1-(N-Butylthiocarbamoyl)vinyl Phosphate

Dimethyl 1-(N-Phenylthiocarbamoyl)vinyl Phosphate

Dimethyl 1-(N-Ethylcarbamoyl)vinyl Thiophosphate

Dimethyl 1-(N-Cyclohexylcarbamoyl)vinyl Thiophosphate

Dimethyl 1-(N-Phenylcarbamoyl)vinyl Thiophosphate

Di-(2-Chloroethyl) 2,2-Dichloro(carbamoyl)vinyl Phosphate

Dimethyl 2,2-Dichloro-1-(N-Methyl-N-phenylcarbamoyl)vinyl Phosphate

Dimethyl 2,2-Dichloro-1-(N-methylcarbamoyl)vinyl Phosphate

Dimethyl 2,2-Dichloro-1-(N-butylcarbamoyl)vinyl Phosphate

Dimethyl 2,2-Dichloro-1-(N-phenylcarbamoyl)vinyl Phosphate

Dimethyl 2,2-Dichloro-1-(N-cyclohexylcarbamoyl)-vinyl Phosphate

Dimethyl 2-Chloro-1-(N-methylcarbamoyl)vinyl Phosphate

Dimethyl 1-(N-Ethylcarbamoyl)vinyl Phosphate

Dimethyl 1-(N-Phenylcarbamoyl)vinyl Phosphate

Dimethyl 1-(N-Cyclohexylcarbamoyl)vinyl Phosphate

Dimethyl 2-Chloro-1-(N-phenylcarbamoyl)vinyl Phosphate
Dimethyl 2-Chloro-1-(N-butylcarbamoyl)vinyl Phosphate
Dimethyl 2-Methylthio-1-(N-ethylcarbamoyl)vinyl Phosphate
Dimethyl 2-Chloro-2-Methylthio-1-(N-butylcarbamoyl)vinyl Phosphate
Dimethyl 2,2-Dichloro-1-(N-methoxy-N-methylcarbamoyl)-vinyl Phosphate
Dimethyl 2-Chloro-1-(N-methoxycarbamoyl)vinyl Phosphate
Dimethyl 2,2-Dichloro-1-(N-allylcarbamoyl)vinyl Phosphate
Dimethyl 2-Chloro-2-chloromethyl-1-(dimethylcarbamoyl)vinyl Phosphate
Dimethyl 2-Chloro-2-bromo-1-(dimethylcarbamoyl)vinyl Phosphate
Dimethyl 2-Bromo-1-(dimethylcarbamoyl)vinyl Phosphate
Dimethyl 2-Fluoro-1-(dimethylcarbamoyl)vinyl Phosphate
Dimethyl 2-Bromo-1-(N-methylcarbamoyl)vinyl Phosphate
Dimethyl 2-Bromo-1-(N-butylcarbamoyl)vinyl Phosphate
Dimethyl 2-Fluoro-1-(N-phenylcarbamoyl)vinyl Phosphate
Dimethyl 2-Chloro-2-(p-chlorophenyl)-1-(N-ethylcarbamoyl)vinyl Phosphate
Dimethyl 2-(2,4,5-Trichlorophenyl)-1-(N-butylcarbamoyl)vinyl Phosphate
Dimethyl 2-Cyano-1-(N-phenylcarbamoyl)vinyl Phosphate
Dimethyl 2-Carbomethoxy-1-(dimethyl carbamoyl)vinyl Phosphate
Dimethyl 2-Chloro-2-acetyl-1-(N-butylcarbamoyl)vinyl Phosphate
Dimethyl 2-Chloro-2-Methylsulfonyl-1-(N-phenylcarbamoyl)vinyl Phosphate
Dimethyl 2,2-Dichloro-1-(N-methyl-N-carbomethoxycarbamoyl)vinyl Phosphate
Dimethyl 2,2-Dichloro-1-(N-acetylcarbamoyl)vinyl Phosphate
Butyl 2-Chloro-1-(N-methylcarbamoyl)vinyl Ethanephosphonate
Methyl 2,2-Dichloro-1-(N,N-dimethylcarbamoyl)vinyl Butane phosphonate In general, the compounds of this invention are prepared by mixing an equivalent amount of a beta-chlorinated alpha-oxocarboxylic acid amide with an appropriate trialkylphosphite in a suitable solvent, i.e. conditions for the Perkow Reaction. The length of time for mixing can vary from one to five hours and the temperature can vary from 0° to 100°C. In most cases, the trialkylphosphite is added to a solution of the chlorinated oxocarboxylic acid amide at a rate sufficient to control the exotherm of the reaction at 30° to 70°C. At the conclusion of the reaction, the solvent is evaporated and pure 1-carbamoylvinyl phosphate is recovered. Appropriate trialkylphosphites, for example trimethylphosphite, are available commercially or can be readily made by known methods. Non-limiting examples of appropriate solvents include benzene, toluene, ethyl ether, hexane and chloroform.

The beta-chlorinated alpha-oxocarboxylic acid amides, some of which are described by Y.A. Cheburkov, et al., Izvest. Akad, Nauk. SSR, 10, 2272(1970) English edition page 2135, are prepared by mixing an appropriate chlorinated carboxylic acid chloride with an appropriate formamide in a suitable solvent (or excess formamide) in the presence of a suitable base such as pyridine, triethylamine, etc. Both the chlorinated carboxylic acid chloride and the formamide are available from normal commercial sources or can be readily prepared by known methods.

The compounds according to the invention may be used in various ways to utilize their insecticidal activity. Accordingly a method of insect control is provided which comprises applying to the insect or to the environment of the insect an insecticidially effective amount of the instant compounds. These compounds can be applied per se, as solids or in vaporized form, but are preferably applied as the toxic components in insect control compositions of the compound and a carrier. The compositions can be applied as dusts, as liquid sprays or as gas propelled sprays and can contain, in addition to the carrier, additives such as emulsifying agents, wetting agents, binding agents, gasses compressed to the liquid state, odorants, stabilizers and the like.

A wide variety of inert liquid and solid carriers can be used in the insect control compositions. Non-limiting examples of liquid carriers include water; organic solvents such as alcohols, ketones, amides and esters; mineral oils such as kerosene, light oils, medium oils; and vegetable oils such as cottonseed oil. Non-limiting examples of solid carriers include talc, bentonite, diatomaceous earth, pyrophyllite, fullers earth, gypsum, flours derived from cottonseeds and nut shells and various natural and synthetic clays.

The amount of the compounds of this invention used in insect control compositions will vary widely. It will depend to some extent upon the type of composition in which the material is being used, the nature of the condition to be controlled, and the method of application (i.e., spraying, dusting, etc.).

As applied in the field, insect control compositions may contain as little as 0.0001 weight percent of the insect control agent. In general, compositions containing about 0.05 weight percent of the insect control agent in either a liquid or solid carrier give excellent results. In some cases, however, stronger dosages up to about 10% by weight may be required.

In practice, insect control compositions are usually prepared in the form of concentrates, which are diluted in the field to the concentration desired for application. For example, the concentrate can be a wettable powder containing large amounts of a compound of this invention, a carrier and a wetting and dispersing agents. Such a powder can be diluted prior to application by dispersing it in water to obtain a sprayable suspension containing the concentration of insect control agent according to the invention desired for application. Other concentrations can be solutions that can be later diluted, e.g., with kerosene. Thus, it is within the scope of this invention to provide insect control compositions containing up to about 80% by weight of the composition, of insect control compounds according to the invention. Therefore, depending upon whether it is ready for application or it is in concentrated form, the insect control compositions of the invention contain between 0.0001 percent and about 80 percent, by weight of the composition, of the insect control compound and an inert solid or liquid carrier, as defined hereinabove.

The following detailed examples are intended as illustrations, rather than limitations, on the scope of this invention so as to provide a better understanding of the nature, objects and advantages of the invention.

EXAMPLE 1

N,N-Dimethyl-3,3,3-trichloropyruvamide

A 273g (1.5 mole) portion of trichloroacetyl chloride was added over one hour to a stirred, cooled (5°C) portion of 330g (4.5 moles) of dimethylformamide. Nitrogen was passed over the solution throughout the reaction. A 152g (1.5 mole) portion of triethylamine was then added dropwise while keeping the temperature below 15°C. The mixture was stirred overnight at ambient temperature and then cooled to 5°C before 300 ml of water was added gradually. The organic products were extracted into ethyl ether, and the ethereal solution was washed with water, 10% hydrochloric acid, and with brine, dried over magnesium sulfate and concentrated. The residue was distilled under vacuum through a short-path still yielding 160g of pure N,N-dimethyl-3,3,3-trichloropyruvamide: Bp 80°–82° (0.2mm); ir($\lambda$max, film) 5.7 (s), 6.0 (s), 9.45 (s), 11.6 (m) microns; nmr ($\delta$, CDCl$_3$) 3.0 and 3.05 (two singlets, 6H) ppm.

EXAMPLE 2

N,N-Diethyl-3,3,3-trichloropyruvamide

The procedure of Example 1 was followed using 27g (0.15 mole) of trichloracetyl chloride and 45g (0.45 mole) of diethyl-formamide and 15g (0.15 mole) of triethylamine. Obtained following distillation was 14g of pure N,N-diethyl 3,3,3-trichloropyruvamide as a clear, colorless liquid: Bp 94°–96° (0.15 mm); ir ($\lambda$max, film) 5.7 (s), 6.1 (s), 6.8 (s), 6.9 (s), 9.4 (s), 12.1 (s) microns.

EXAMPLE 3

N,N-Dimethyl-3,3-dichloro-2-oxobutyramide

The procedure of Example 1 was followed using 32g (0.2 mole) of 2,2-dichloropropionyl chloride and 44g (0.6 mole) of dimethylformamide and 20g (0.2 mole) of triethylamine. Obtained following distillation was 12g of pure N,N-dimethyl-3,3-dichloro-2-oxobutyramide as a clear, colorless liquid: Bp: 68°–70° (0.2mm); ir ($\lambda$max, film) 5.7 (s), 6.1 (s), 7.1 (s), 9.3 (s), 9.9 (s), 12.6 (s) microns.

EXAMPLE 4

Dimethyl 2,2-Dichloro-1-(dimethylcarbamoyl)vinyl Phosphate

A 41g sample of freshly distilled trimethylphosphite was added dropwise to a stirred solution of 73g of Example 1 in 600 ml of dry ethyl ether. A gradual flow of nitrogen was passed over the solution throughout the reaction. The reaction was exothermic and the rate of addition was adjusted to allow a gentle reflux of the ethereal solution. The reaction solution was stirred for 0.5 hr following addition and then concentrated finally under low vacuum at ambient temperature. Obtained was 95g of pure dimethyl 2,2-dichloro-1-dimethylcarbamoylvinyl phosphate as a clear, colorless liquid residue: ir ($\lambda$max, film) 6.07 (s), 7.7 (s), 11.6 (s) microns; nmr ($\delta$, CCl$_4$), 2.85 (s, 3H), 2.98 (s, 3H), 3.69 (d, 6H) ppm.

EXAMPLE 5

Diethyl 2,2-Dichloro-1-(dimethylcarbamoyl)vinyl Phosphate

The procedure of Example 4 was followed using 55g of freshly distilled triethylphosphite and 73g of Example 1 in 600 ml of dry ethyl ether. Obtained was 106g of pure diethyl 2,2dichloro-1-dimethyl-carbamoylvinyl phosphate as a clear, colorless liquid residue: ir ($\lambda$max, film) 6.1 (s), 7.7 (s), 9.6 (s), 11.6 (s) microns; nmr ($\delta$ CDCl$_3$) 1.34 (t,6H), 3.1 (s, 3H), 4.2 (m,4H) ppm.

EXAMPLE 6

Dimethyl 2,2-Dichloro-1-(diethylcarbamoyl)vinyl Phosphate

The procedure of Example 4 was followed using 2.3g of trimethylphosphite and 4.6g of Example 2 in 25 ml of dry ether. Obtained was 5.2g of pure dimethyl 2,2-dichloro-1-diethyl-carbamoylvinyl phosphate as a clear, colorless liquid residue: ir ($\lambda$max, film) 6.1 (s), 7.7 (s), 9.6 (s), 11.6 (s) microns; nmr ($\delta$, CCl$_4$) 1.14 (m,6H), 3.3 (m, 4H), 3.67 (d, 6H) ppm.

EXAMPLE 7

Dimethyl 2-Chloro-2-methyl-1-(dimethylcarbamoyl)vinyl Phosphate

The procedure of Example 4 was followed using 2.5g of tri-methylphosphite and 4.0g of Example 3 in 35 ml of dry ether. Obtained was 5.4g of pure dimethyl 2-chloro-2-methyl-1-di-methylcarbamoylvinyl phosphate as a clear, colorless liquid residue: ir ($\lambda$max, film) 6.1 (s), 7.75 (s), 9.5 (s), 10.6 (s), 11.4 (s), 11.7 (s) microns; nmr ($\delta$, CCl$_4$) 2.07 (d, 3H), 2.89 (s, 3H), 2.97 (s, 3H), 3.7 (d, 6H) ppm.

EXAMPLE 8

Diethyl 2-Chloro-2-methyl-1-(dimethylcarbamoyl)vinyl Phosphate

The procedure of Example 4 was followed using 3.3g of triethylphosphite and 4.0g of Example 3 in 35 ml of dry ether. Obtained was 6.0g of pure diethyl 2-chloro-2-methyl-1dimethylcarbamoylvinyl phosphate as a clear, colorless liquid residue: ir ($\lambda$max, film) 6.08 (s), 7.2 (s), 7.8 (s), 9.7 (s), 11.4 (s), 12.5 (s) microns; nmr ($\delta$CCl$_4$) 1.26 (t, 6H), 1.99 (d, 3H), 2.81 (s, 3H), 2.91 (s, 3H), 3.99 (m, 4H) ppm.

EXAMPLE 9

N,N-Dimethyl-3,3-dichloropyruvamide

A mixture of 26.2g (0.12 mole) of example 1 and 0.2g of platinum oxide in 200 ml of absolute ethanol was shaken under 30 to 10 lbs of hydrogen on a Parr Apparatus until the uptake ceased at 0.12 moles of hydrogen. The hydrogenation was rapid (ca. 30 min.) and moderately exothermic. Additional agitation under 30 lbs. of hydrogen for 30 min. resulted in no hydrogen uptake. The mixture was filtered, and the filtrate was concentrated. The residue was mixed with 100 ml of ether and magnesium sulfate, and the organic solution was filtered and concentrated to afford 19g of a clear, yellow liquid. Shortpath distillation afforded 14g of pure example 9: Bp 91°–92° (3.0 mm); ir (film) 3.4 (s), 5.8 (s), 6.1 (s), 7.2 (m), 9.7 (m), 12.2 (m) microns; nmr (CDCl$_3$) 6.86 (1H, S), 3.02 and 3.08 ( 6H, d) ppm.

Anal. Calcd for $C_5H_7Cl_2NO_2$: C,32.64; H,3.81. Found: C,32.91; H,3.78.

EXAMPLE 10

Dimethyl 2-Chloro-1-(dimethylcarbamoyl)vinyl Phosphate

A 2.4g (0.02 mole) sample of trimethylphosphite was added portionwise to a solution of 3.7g (0.02 mole) of example 9 in 30 ml of benzene so as to control the exotherm at 30° to 40°C. The reaction solution was stirred for 0.5 hr at 35°C following addition and then concentrated finally under low vacuum at ambient temperature. Obtained was 4.1g of pure example 10 as a clear, colorless liquid: ir(film) 3.4 (m), 6.05 (s), 7.75 (s), 9.5 (s, broad) microns; nmr (CDCl$_3$) 6.21 (1H, s), 3.91 and 3.30 (6H, d), 3.05 (6H, s) ppm.

EXAMPLE 11

Diethyl 2-Chloro-1-(dimethylcarbamoyl)vinyl Phosphate

A 3.3g (0.02 mole) sample of triethylphosphite was added to 3.7g (0.02 mole) of example 9 in the same manner as for example 10. Obtained was 5.3g of pure example 11 as a clear, colorless liquid: ir (film) 3.4 (m), 6.05 (s), 7.8 (s), 9.7 (s, broad) microns; nmr (CDCl$_3$) 6.20 (1H,s), 4.25 (4H, quintet), 3.05 (6H,S), 1.34 (6H,t) ppm.

EXAMPLE 12

N,N-Dimethyl-3-Chloropyruvamide

A. A mixture of 13.1g (0.06 mole) of the titled compound of example 1 and 0.2g of platinum oxide in 110 ml of 85% aqueous ethanol was shaken under 30 to 10 lbs. of hydrogen on a Parr Apparatus until the uptake ceased at 0.12 moles of hydrogen. Continued shaking under 30 lbs. of hydrogen did not result in hydrogen uptake. The reaction was rapid (Ca. 50 Min) and slightly exothermic. The mixture was filtered, and the filtrate was concentrated. The residue was mixed with 100 ml of ether and magnesium sulfate, and the organic solution was filtered and concentrated to afford 6.1g of a light yellow liquid. Glpc analysis indicated 96% of one product. The residue was combined with part B for distillation.

B. A mixture of 35g (0.19 mole) of the titled compound of example 9 and 0.2g of platinum oxide in 200 ml of 90% aqueous ethanol was shaken under 30 10 lbs of hydrogen on a Parr Apparatus until the uptake ceased. The consumption of 0.2 moles of hydrogen required 3.5 hrs. The mixture was processed as in part A to afford 27g of a liquid (98% by glpc). The combined products from parts A and B were distilled through a short-path apparatus to provide 26.4g of pure example 12: Bp 87°–89° (3.0 mm); ir (film) 3.4 (s), 5.8 (s), 6.1 (s), 7.15 (s), 9.4 (s), 9.6 (s) u; nmr (CDCl$_3$) 4.51 (2H, s), 3.0 and 3.06 (6H, d) ppm.

Anal. Calcd for $C_5H_8ClNO_2$ : C, 40.15; H, 5.39. Found: C, 40.03; H, 5.51.

EXAMPLE 13

Dimethyl 1-(N,N-Dimethylcarbamoyl)vinyl Phosphate

The procedure of example 10 was followed for the reaction of 3.6g (0.03 mole) of trimethylphosphite with 4.5g (0.03 mole) of the titled compound of example 12 in 30 ml of benzene. Obtained was 6.7g of example 13 as a clear, colorless liquid : ir (film) 3.4 (m), 6.1 (s), 7.8 (s), 9.6 (s, broad), 11.6 (m) microns; nmr (CDCl$_3$) 5.33 and 5.10 (2H, two multiplets), 3.88 and 3.77 (6H,d), 3.05 (6H, broad s) ppm.

EXAMPLE 14

Diethyl 1-(N,N-Dimethylcarbamoyl)vinyl Phosphate

The procedure of example 10 was followed for the reaction of 3.3g (0.02 mole) of triethyl phosphite with 3.0g (0.02 mole) of the titled compound of example 12 in 30 ml of benzene. Obtained was 5.1g of pure example 14 as a clear, colorless liquid : ir (film) 3.4 (m), 6.1 (s), 7.8 (s), 9.7 (s, broad), 12.0 (s) microns; nmr (CDCl$_3$) 5.37 and 5.10 (2H, two multiplets), 4.20 (4H, quintet), 3.02 (6H, broad s), 1.35 (6H, t) ppm.

EXAMPLE 15

N,N-Dimethyl 3-Chloro-2-oxobutyramide

The procedure of example 12 was followed for the hydrogenation of 9.9g (0.05 mole) of the titled compound of example 3 using 0.2g of platinum oxide and 100 ml of 90% aqueous ethanol. The hydrogen uptake was rapid (35 min) and then ceased at 0.05 mole consumed. Obtained following work-up was 8.3g of a yellow liquid. The procedure was repeated and the combined products were distilled through a 4 in. Vigreaux column to afford 12g of pure example 15 : Bp 84°–85° (3.0 mm); ir (film) 3.4 (m), 5.8 (s), 6.1 (s), 8.0 (m), 9.3 (m), 12.5 (m) microns; nmr (CDCl$_3$) 5.15 (1H, q), 3.05 6H,s), 1.65 (3H, d)ppm.

Anal. Calcd for $C_6H_{10}ClNO_2$ : C.44.05; H, 6.16. Found: C, 43.88; H, 6.23.

EXAMPLE 16

Dimethyl 2-Methyl-1-(N,N-dimethylcarbamoyl)vinyl Phosphate

The procedure of example 10 was followed for the reaction of 2.4g (0.02 mole) of trimethylphosphite with 3.2g (0.02 mole) of the titled compound of example 15 in 30 ml of benzene. Obtained was 3.8g of pure the titled compound of example 16 as a clear, colorless liquid : ir (film) 3.5 (m), 6.1 (s), 7.8 (s), 9.5 (s, broad), 11.7 (m) microns; nmr (CDCl$_3$) 5.65 (1H, multiplet), 3.38 and 3.27 (6H, doublet), 3.03 6H, s), 1.78 (3H, multiplet) ppm.

EXAMPLE 17

N,N-Dimethyl-3,3,3-trichloro-1-thiopyruvamide

The procedure of Example 1 was followed using 25g (0.14 mole) of trichloroacetyl chloride, 25g (0.28 mole) of N,N-dimethyl-thioformamide and 15g (0.15 mole) of triethylamine. Following work-up and distillation, there was obtained 6.9g of colorless liquid: b.p. 122°–124° (0.5mm); ir ($\lambda$max, film) 5.7 (s), 6.5 (s), 7.15 (s), 8.8 (s), 11.75 (s), 13.4 (s) microns; nmr ($\delta$ ,CCl$_4$) 3.23 (3H,s) and 3.32 (3H,s)ppm. The product solidified on standing; m.p. 52°–56°.

EXAMPLE 18

Dimethyl 2,2-dichloro-1-(dimethylthiocarbamoyl)vinyl Phosphate

The procedure of Example 4 was followed using 2.3g of trimethyl phosphite and 4.7g of the titled compound of Example 17 in 30 ml of dry ether. There was obtained a quantitative yield of reddish product: ir ($\lambda$max, film) 6.6 (s), 7.8 (s), 918 (s) microns; nmr ($\delta$ ,CCl$_4$)

3.3 (6H,s), 3.6 (3H,d), 3.78 (3H,d)ppm.

EXAMPLE 19

Diethyl 2,2-dichloro-1-(dimethylthiocarbamoyl)vinyl Phosphate

The procedure of Example 4 was followed using 1.3g of tri-ethylphosphite and 1.8g of the titled compound of Example 17 in 10 ml of dry ether. There was obtained a quantitative yield of amber product: ir (λmax, film) 3.4 (s), 6.6 (s), 7.2 (s), 7.8 (s), 8.7 (s), 9.8 (s), microns.

EXAMPLE 20

N,N-Dimethyl 2-Methylmercaptopyruvamide

A solution of 5.0g (0.05 mole) of triethylamine in 50 ml of acetone was saturated with methylmercapton and added dropwise at 0°C to a stirred solution of 7.5g (0.05 mole) of the titled compound of Example 12 in 20 ml of acetone. The mixture was stirred at ambient temperatures for 2 hrs. and then filtered. The filtrate was concentrated and the residue was mixed with ether and magnesium sulfate. The solution was filtered and concentrated to afford 5.2g of pure Example 20 as a clear, orange liquid: ir (film) 3.4 (m), 5.8 (s), 6.1 (s), 7.2 (m), 8.2 (m), 9.5 (s) microns; nmr (CDCl$_3$) 3.5 (2H,s), 3.06 and 3.0 (6H,d), 2.08 (3H,s) ppm.

EXAMPLE 21

Dimethyl 2-Methylmercapto-1-(N,N-dimethylcarbamoyl)vinyl Phosphate

The procedure of Example 10 was followed for the reaction of 2.9g (0.022 mole) of trimethylphosphite with 3.2g (0.02 mole) of the titled compound of Example 20 in 20 ml of bromotrichloromethane. After heating for 1 hr. at 50°C, the reaction solution was concentrated to afford 4.2g of pure Example 21 as a brown, clear liquid: ir (film) 3.4 (m), 6.1 (s), 7.8 (s), 9.6 (s, broad), 11.7 (m) microns; nmr (CDCl$_3$) 6.22 (1H, multiplet), 3.7 (6H, multiplet), 3.03 (6H, broad, s), 2.35 and 2.10 (3H,d) ppm.

Example 1 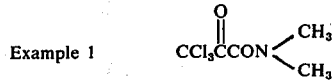

Example 2 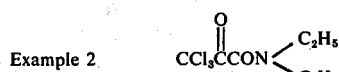

Example 3 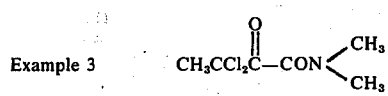

Example 4 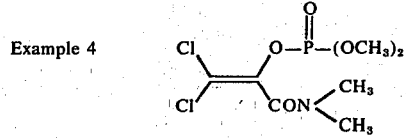

Example 5 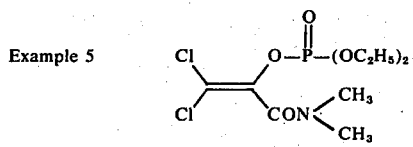

Example 6 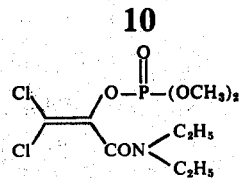

Example 7 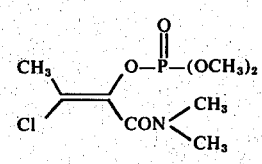

Example 8 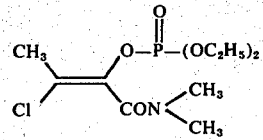

Example 9 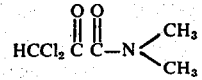

Example 10 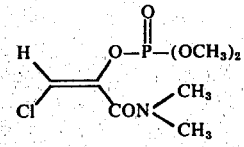

Example 11 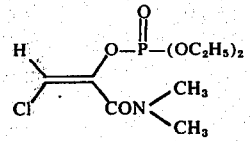

Example 12 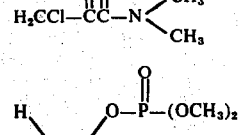

Example 13 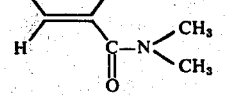

Example 14 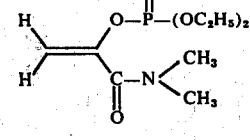

Example 15 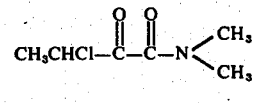

Example 16 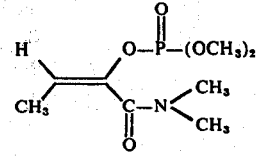

Example 17 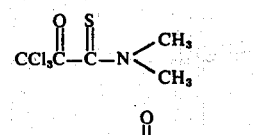

Example 18 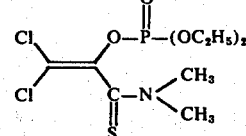

Example 19 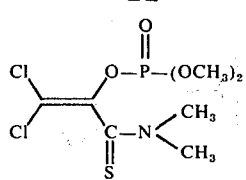

Example 20 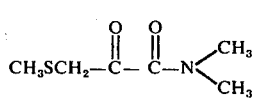

Example 21 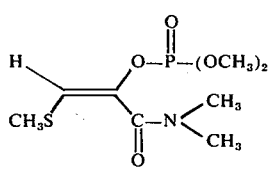

EXAMPLE 22

1-Carbamoylvinyl phosphates of this invention were evaluated in standard greenhouse contact spray insecticide tests using housefly (HF), German cockroach (GC), boll weevil (BW) and bean aphid (BA). Adult insects (the BA via aphid-infested Nasturtium leaves) were confined in specially designed 100 mm petri dish screened cages and exposed to sprays at 15 psi of 10.0 − 20.0 ml of an acetone solution of the test material. The test cages were mounted on a turntable rotating at 30 rpm in a wind tunnel for HF and BA and in hoods for GC and BW. All tests were run in duplicate using 10 insects respectively per cage. All tests were conducted in comparison with a standard insecticide; diazinon for HF and GC a methyl parathion for BW and malathion for BA. After being sprayed the cages were furnished with a supply of food to avoid the occurrence of natural mortality.

Mexican bean Beetle (MB) was subjected to the following stomach poison dip test: Lima bean leaves of a uniform size were momentarily dipped in a water-acetone solution of the test material. When dry, the petiole of the treated leaf was placed in a water-filled plastic container on a specially constructed holding stand in order to keep it turgid for the duration of the evaluation. Five third or fourth instar larvae are introduced and encouraged to feed on the treated foliage by means of confinement. Each treatment is replicated two times. Dursban is the standard material for comparison.

Mortaility was recorded for GC at 24 and 48 hours after exposure, for HF, BW and MB at 24 hours with a knockdown count for HF after 60 minutes.

The rate of application was 500 ppm and 1000 ppm of active ingredient. The results as set forth in the Table below indicate the percent kill of the test insects.

| Active Ingredient | Test Insects | | | | |
|---|---|---|---|---|---|
| | HF | GC | BW | MB | BA |
| Example 4[a] | 100 | 100 | 100 | 100 | 100 |
| Example 5[a] | 100 | 100 | 100 | 100 | 100 |
| Example 6[a] | 100 | 60 | 100 | 100 | 100 |
| Example 7[b] | 60 | — | — | 100 | 100 |
| Example 8[b] | 60 | — | — | 100 | 100 |
| Example 10[a] | 100 | 80 | 100 | 100 | 100 |
| Example 11[a] | 100 | 70 | 100 | 100 | 100 |
| Example 13[a] | 100 | 20 | 20 | 100 | 100 |
| Example 14[a] | 100 | 80 | — | 100 | 100 |
| Example 16[a] | 20 | — | — | 60 | 100 |
| Example 18[a] | 100 | 80 | 60 | 100 | 100 |
| Example 19[a] | 60 | — | 70 | 100 | 100 |

-continued

| Active Ingredient | Test Insects | | | | |
|---|---|---|---|---|---|
| | HF | GC | BW | MB | BA |
| Example 21[a] | 20 | 10 | 40 | 60 | 100 |

[a] 500 ppm
[b] 1000 ppm

From the data set forth in the Table, it will be noted that the compounds according to the invention are highly effective insecticides functioning both as contact and stomach poisons.

EXAMPLE 23

1-Carbamoylvinyl phosphates of this invention were evaluated as follows in standard greenhouse systemic insecticide tests using Mexican Bean Beetle (MB) and Bean Aphid (BA).

BEAN APHID (BA)

Young lima bean seedlings growing in a sand-soil medium are removed and the roots thoroughly washed. The roots of the seedlings are immersed immediately in test tubes containing a nutrient solution containing 50 ppm concentration of the material under test. Three days later, the seedlings are infested with 10 adult aphids by careful transfer with a camel's hair brush. Each treatment is replicated two times. The per cent mortality is recorded 48 hours after the seedlings are infested.

MEXICAN BEAN BEETLE (MB)

Similar to the method described for the bean aphid, except that 5 fourth instar larvae are used. The results of these tests as set forth in the following Table indicate the per cent kill of the test insects.

| Active Ingredient | BA | MB |
|---|---|---|
| Example 10 | 100 | 100 |
| Example 11 | 100 | 100 |
| Example 13 | 100 | 100 |
| Example 16 | 90 | 10 |
| Example 18 | 40 | 60 |
| Example 19 | 10 | 10 |
| Example 21 | 100 | 100 |

From the data set forth in the Table, it will be noted that the compounds of this invention have systemic insecticide activity, as well as contact and stomach poison effectiveness.

Although the present invention has been described with preferred embodiments, it is to be understood that modifications and variations may be resorted to, without departing from the spirit and scope of this invention, as those skilled in the art will readily understand. Such variations and modifications are considered to be within the purview and scope of the appended claims.

What is claimed is:

1. A compound having the following general formula:

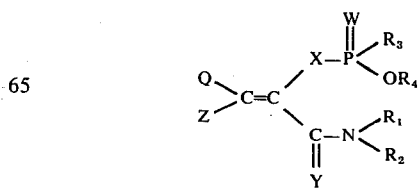

where X, Y and W are oxygen or sulfur, and $R_1$, $R_2$, $R_3$ and $R_4$ are each a radical selected from the group consisting of hydrogen, branched or unbranched alkyl ($C_1$–$C_8$), cycloalkyl ($C_3$–$C_8$), alkenyl ($C_2$–$C_8$), alkoxy ($C_1$–$C_8$), aryl, aralkyl ($C_7$–$C_{14}$), acetyl, carbalkoxy, alkylmercapto ($C_1$–$C_8$), carbamoyl (mono and dialkyl) and combinations thereof and which radical may have substituted thereon a member or members of the group consisting of hydroxy, halogen, alkoxy, cyano, carbalkoxy and combinations and multiples thereof and Q and Z are selected from the group consisting of $R_1$, $R_2$, $R_3$ and $R_4$ or from the group consisting of halogen (Cl, Br, F), cyano and alkylsulfonyl.

2. A compound of claim 1, wherein said compound is dimethyl 2,2-dichloro-1-(dimethylcarbamoyl)vinyl phosphate.

3. A compound of claim 1, wherein said compound is diethyl 2,2-dichloro-1-(dimethylcarbamoyl)vinyl phosphate.

4. A compound of claim 1, wherein said compound is dimethyl 2,2-dichloro-1-(diethylcarbamoyl)vinyl phosphate.

5. A compound of claim 1, wherein said compound is dimethyl 2-chloro-1-(dimethylcarbamoyl)vinyl phosphate.

6. A compound of claim 1, wherein said compound is diethyl 2-chloro-1-(dimethylcarbamoyl)vinyl phosphate.

7. A compound of claim 1, wherein said compound is dimethyl 1-(N,N-dimethylcarbamoyl)vinyl phosphate.

8. A compound of claim 1, wherein said compound is diethyl 1-(N,N-dimethylcarbamoyl)vinyl phosphate.

9. A compound of claim 1, wherein said compound is dimethyl 2,2-dichloro-1-(dimethylthiocarbamoyl)vinyl phosphate.

10. A compound of claim 1, wherein said compound is dimethyl 2-methylmercapto-1-(N,N-dimethylcarbamoyl)vinyl phosphate.

* * * * *